US00PP36422P3

(12) United States Plant Patent
van Zoelen

(10) Patent No.: US PP36,422 P3
(45) Date of Patent: Feb. 4, 2025

(54) ***CORYLUS* PLANT NAMED 'BWM01'**

(50) Latin Name: *Corylus avellana*
Varietal Denomination: BWM01

(71) Applicant: Brigitta Wilhelmina Maria van Zoelen, Boskoop (NL)

(72) Inventor: Brigitta Wilhelmina Maria van Zoelen, Boskoop (NL)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 18/085,187

(22) Filed: Dec. 20, 2022

(65) Prior Publication Data

US 2024/0206359 P1 Jun. 20, 2024

(51) Int. Cl.
*A01H 5/08* (2018.01)
*A01H 6/00* (2018.01)

(52) U.S. Cl.
USPC ..... Plt./152
CPC ..... *A01H 6/00* (2018.05)

(58) Field of Classification Search
USPC ..... Plt./152, 216
CPC ..... A01H 5/0825
See application file for complete search history.

(56) References Cited

PUBLICATIONS https://www.boom-in-business.nl/upload/artikelen/bib3nieuweenpopluaireheesters.pdf; Mar. 2021; 2 pages.*
https://breederplants.nl/en/sortiment; Oct. 12, 2023; 2 pages.*

* cited by examiner

*Primary Examiner* — Kent L Bell
(74) *Attorney, Agent, or Firm* — Weatherly IP Solutions, LLC; James M. Weatherly; Karen P. Bechtold

(57) ABSTRACT

A *Corylus* tree particularly distinguished by a fast growing upright habit and a leaf color of greyed-purple, black, purple and brown, is disclosed.

4 Drawing Sheets

Genus and species: *Corylus avellana.*
Varietal denomination: 'BWM01'.

BACKGROUND OF THE NEW PLANT

The present invention comprises a new and distinct variety of Hazel, botanically known as *Corylus avellana*, and hereinafter referred to by the variety name 'BWM01'.

'BWM01' is the result of an open pollination at the breeder's nursery in Boskoop, Netherlands, where the female parent was the *Corylus avellana* named 'Maxima Purpurea' (unpatented) and an unknown male parent. Seeds were found in 2012 and sown in Boskoop, Netherlands. A seedling from the seed planted from the open pollination was discovered by the breeder at his nursery in October 2015 and named 'BWM01'. In the summer of 2016, 'BWM01' was first propagated by cuttings. 'BWM01' was found to reproduce true to type in successive generations of asexual propagation via cuttings in Boskoop, Netherlands.

SUMMARY

The following are the most outstanding and distinguishing characteristics of this new variety when grown under normal horticultural practices in Boskoop, Netherlands.

1. A fast upright growing habit; and
2. Leaf color of greyed-purple, black, purple and brown.

DESCRIPTION OF THE PHOTOGRAPH

This Hazel tree is illustrated by the accompanying photographs. The photographs are of an 18-month-old plant grown in a field in Boskoop, Netherlands in October of 2022. The colors shown are as true as can be reasonably obtained by conventional photographic procedures.

DESCRIPTION OF THE NEW VARIETY

Figure 1:
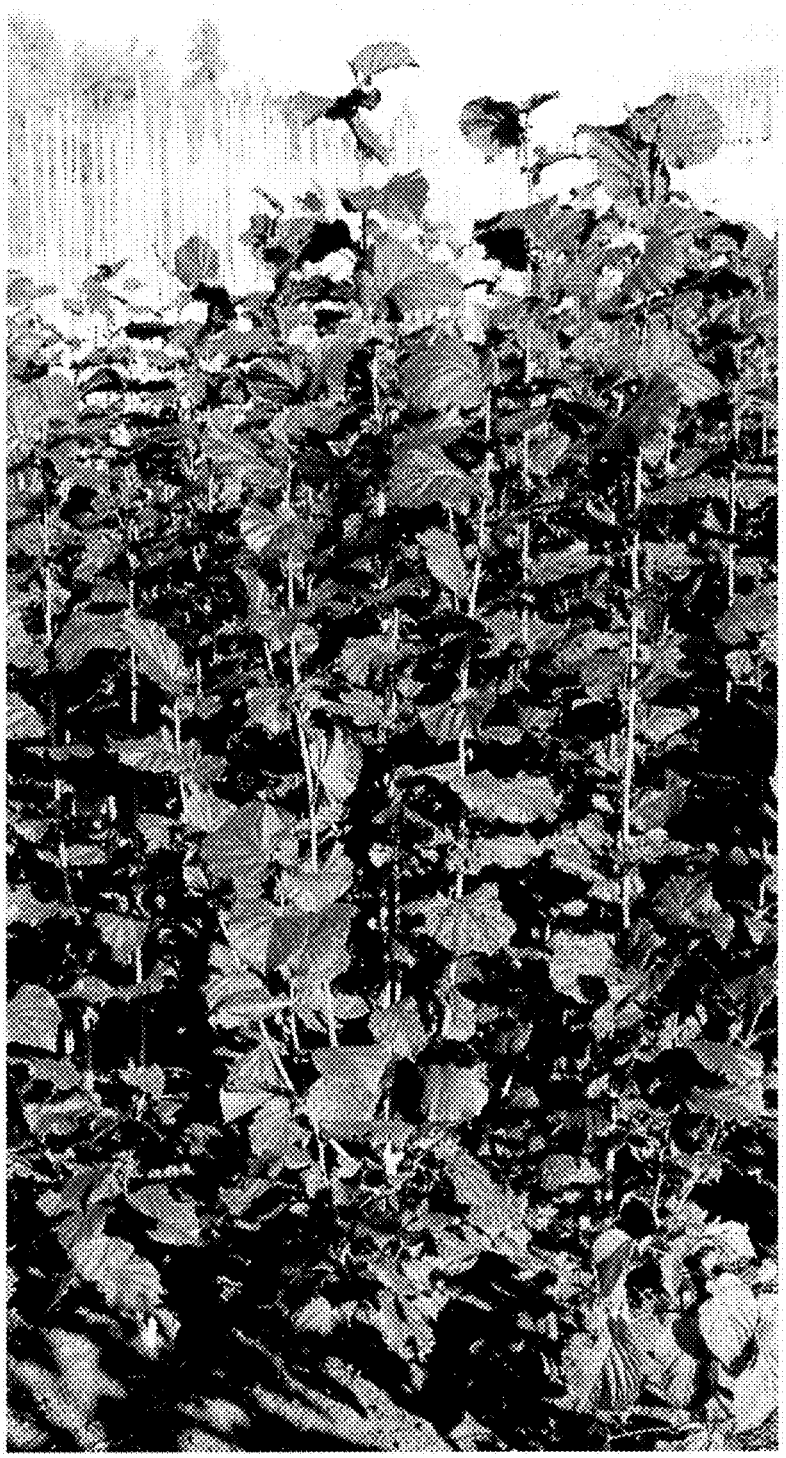
FIG. 1 is a photograph showing the entire plant of 'BWM01'.
Figure 2:
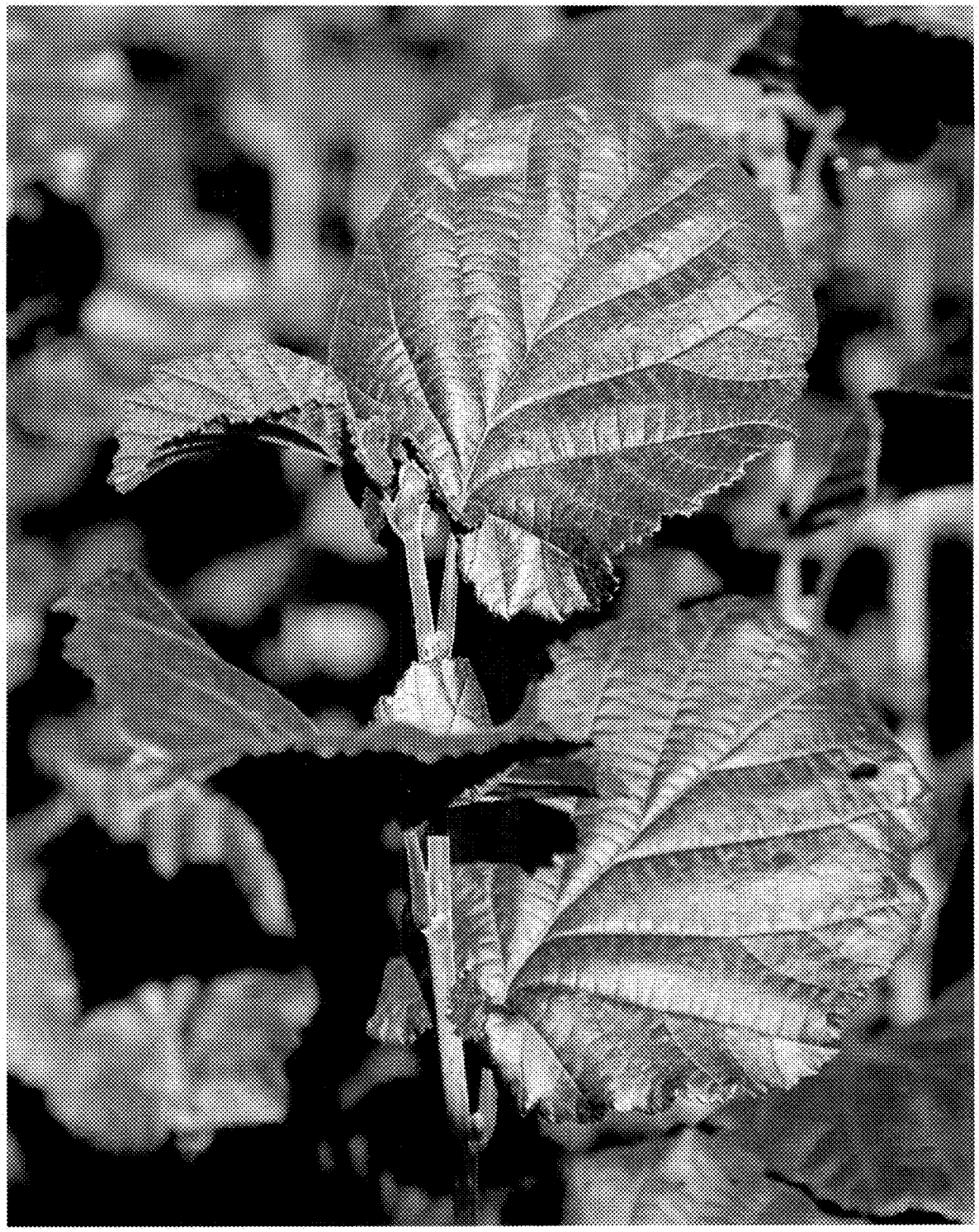
FIG. 2 is a photograph of the upper side of the foliage of 'BWM01'.
Figure 3:
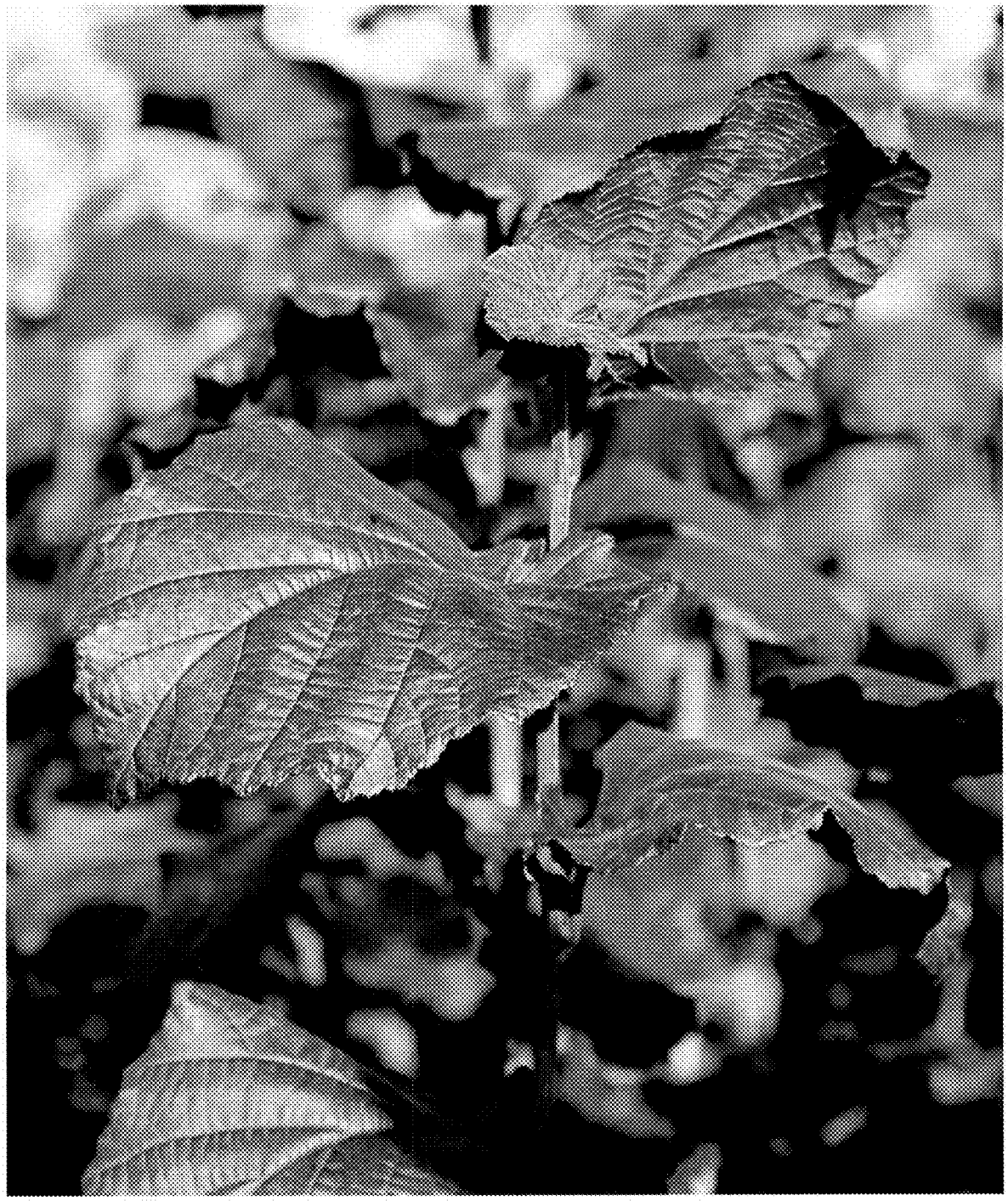
FIG. 3 is a photograph of the under side of the foliage of 'BWM01'.
Figure 4:
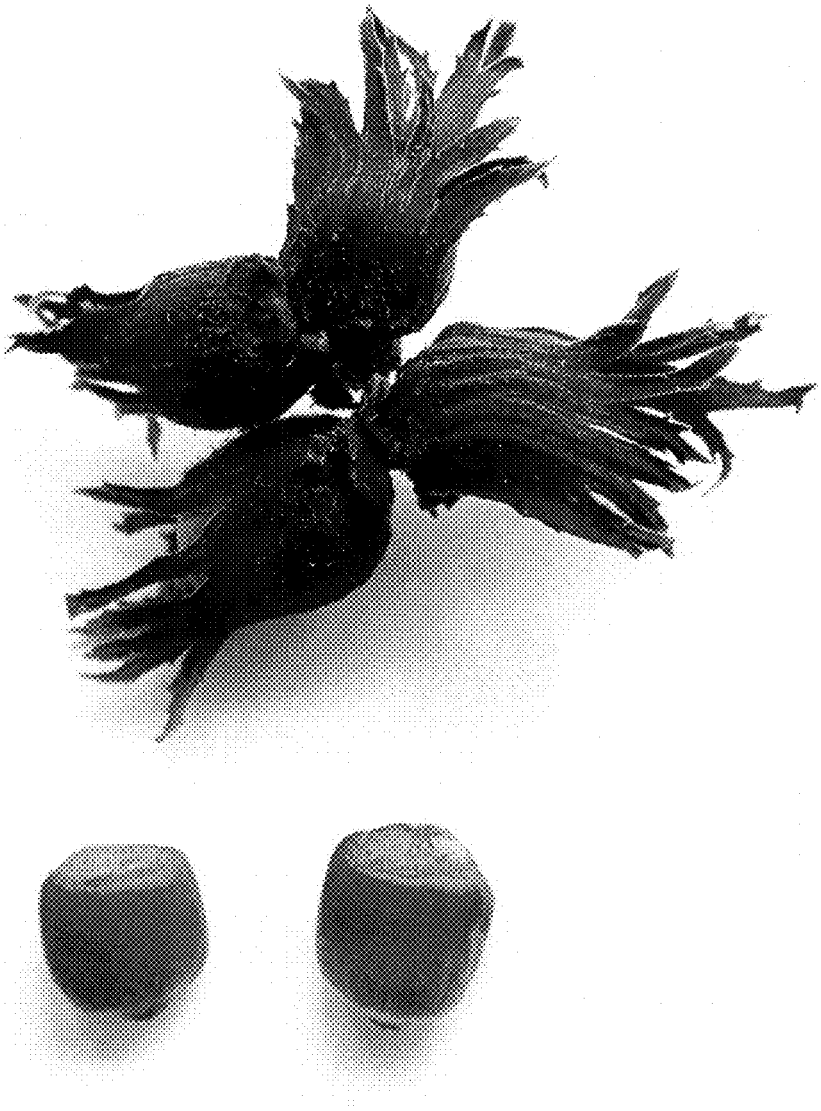
FIG. 4 is a photograph showing the fruit of 'BWM01'.

The following detailed descriptions set forth the distinctive characteristics of 'BWM01'. The data which define these characteristics were collected from asexual reproductions carried out in Boskoop, Netherlands. Data was collected on 18-month-old plants grown in a field in Boskoop, Netherlands in October of 2022. Color references are to The R.H.S. Colour Chart of The Royal Horticultural Society of London (R.H.S.), 6$^{th}$ edition (2015), unless otherwise noted.

Classification:
*Family.*—Betulaceae.
*Botanical.*—*Corylus avellana.*
*Common.*—Hazel.
*Designation.*—'BWM01'.

Parentage:
*Female parent.*—*Corylus avellana* Maxima Purpurea.
*Male parent.*—Unknown.

Growth:
*Propagation type.*—By cuttings.
*Growth habit.*—Broad upright.
*Vigor.*—Very vigorous.
*Height.*—Average 200 cm up to 800 cm.

*Width*.—Average 95 cm up to 250 cm.

*Time to produce a finished flowering plant*.—Approximately 48 months.

Lateral branches:

*Quantity of stems per plant*.—3 main stems.

*Branching habit*.—Main stem grows from base with lateral branches.

*Length*.—Average 127.5 cm.

*Diameter*.—Average 0.8 cm.

*Internode length*.—Average 5.8 cm.

*Texture and appearance*.—Developing stems are matte and mature stems are moderately glossy.

*Color*.—Developing (young): RHS N186C and RHS 200B, at the tips of shoots. Developed (mature): RHS 199C.

Leaves:

*Arrangement*.—Alternate.

*Length*.—Average 13.8 cm.

*Width*.—Average 11.6 cm.

*Shape*.—Broad ovate to near broad ovate.

*Apex*.—Short articulate.

*Base*.—Cordate, lobes free to slightly overlapping.

*Margin*.—Irregular bicrenate-serrate.

*Texture and appearance*.—Upper surface: Non-rugose and slightly to moderately glossy. Lower surface: Slightly rugose and very slightly glossy.

*Venation pattern*.—Pinnate.

*Venation color*.—Upper surface: RHS 181A. Lower surface: RHS 178A and 178B.

*Color, developing leaves*.—Upper surface: Slightly darker than a blend of RHS N186C and 200A. Lower surface: RHS N186C.

*Color, fully expanded leaves*.—Upper surface: Slightly darker then RHS N186A and 203A, fall lower leaves fade to yellow-green darker than 147A. Lower surface: Slightly lighter than a blend of RHS N77A and 200B, fall lower leaves fade to yellow-green darker than 148A.

*Petiole*.—Length: Average 2.4 cm. Diameter: Average 0.3 cm. Texture and appearance (both upper and lower surfaces): Smooth and glabrous. Color: Upper part: RHS N186C. Lower part: RHS N186C.

Inflorescence:

*Arrangement*.—Flowers monoecious; male flowers in catkins, female flowers bud-like, in pairs.

*Inflorescence type and form*.—Single; male flowers in catkins, female flowers bud-like, in pairs.

*Inflorescence height*.—Average length of male inflorescences: 7.4 cm.

*Inflorescence diameter*.—Average diameter of male inflorescences: 0.8 cm.

*Quantity of flowers per inflorescence*.—Average number of male flowers per plant: 225. Average number of female flowers per plant: 400 pairs.

*Quantity of flowers per plant*.—Average quantity of male flowers per plant: 225. Average number of female flowers per plant: 400 pairs.

*Quantity of flower buds per plant*.—Average quantity of male flower buds per plant: 40. Average number of female flower buds per plant: 40.

*Quantity of flowers and flower buds per plant*.—Average quantity of male flowers per plant: 265. Average number of female flowers per plant: 440 pairs.

*Natural flowering season*.—Late winter into early spring.

*Time to flower or response time*.—Average: 10 months.

Flower bud:

*Flower bud length*.—Average length of bud (immature inflorescence) holding male flowers: 2.9 cm. Female flowers enclosed in leaf-buds, not measurable.

*Flower bud diameter*.—Average diameter of bud (immature inflorescence) holding male flowers: 0.5 cm. Female flowers enclosed in leaf-buds, not measurable.

*Flower bud shape*.—Bud (immature inflorescence) holding male flowers cylindrical. Female flowers enclosed in ovate leaf-buds.

*Flower bud texture*.—Buds of male flowers very short moderately pubescent on undersides of scales, average length 0.2 mm, colored greyed-white; too small and too sparsely present to be measured with RHS-CC. Buds of female flowers glabrous.

*Flower bud luster*.—Buds of male and female flowers matte.

*Flower bud color*.—Male flowers (catkins) grey; RHS 201B, slightly tinged purple; RHS N77C. Female flowers (buds) brown; RHS 200B.

Flower:

*General information*.—No corolla or calyx present. Male flowers: Consisting of a single scale, holding 2 bracts and 8 anthers. Scale shaped rhomboidal, apex broad abruptly acute, base cuneate. Average length: 0.4 cm. Average diameter: 0.25 cm. Lower half on upper side smooth and rugose. Upper half on upper side pubescent with very short adpressed hairs, average length approx. 0.1 mm, colored grey-brown; RHS 199D. Upper side of scale colored greyed-purple; RHS 183D. Under side of scale smooth and glabrous, colored greyed-purple; RHS 183D and slightly lighter. Bracts broad deltoid apex broad acute, base broad cuneate. Average length: 0.2 cm. Average diameter; 0.15 cm. Upper side moderately pubescent with very short adpressed hairs, average length approx. 0.1 mm, colored grey-brown; RHS 199D. Upper side of scale colored greyed-purple; RHS 183D. Under side of scale smooth and glabrous, colored greyed-purple; 183D and slightly lighter. Female flowers visibly consisting of two styles only.

Peduncle: Male catkins on peduncles, female flowers bud-like, sessile.

*Terminal peduncle length*.—Average: 7.2 cm.

*Terminal peduncle diameter*.—Average: 0.2 cm.

*Peduncle angle to lateral branch axis*.—Average: 45°, peduncle curved downward in an average angle of 90° to soil level.

*Peduncle strength*.—Strong.

*Peduncle texture*.—Densely pubescent with short, woolly pubescence, average length of hairs: 0.2 mm, colored grey-brown; RHS 199C.

*Peduncle luster*.—Matte.

*Peduncle color*.—Grey-brown; 199A.

Reproductive organs:

*Number of stamen per flower*.—Average: 8.

*Filament length*.—Average: 0.05 cm.

*Filament color*.—Greyed-green; RHS 197C and RHS 197D.

*Anther shape*.—Broad ovate, basifixed.

*Anther length*.—Average: 0.08 cm.
*Anther width*.—Average: 0.06 cm.
*Anther color*.—Greyed-purple; RHS 187B.
*Amount of pollen*.—Low.
*Pollen color*.—Yellowish white; close to RHS 158D and lighter.
*Pistil number* (*per flower*).—Average: 2.
*Pistil length*.—Average: 0.2 cm.
*Stigma shape*.—Pointed.
*Stigma length*.—Average: 0.3 mm.
*Stigma diameter*.—Average: 0.3 mm.
*Stigma color*.—Greyed-purple; RHS N186C.
*Style length*.—Average: 0.17 cm.
*Style color*.—Greyed-purple; 187A.
*Ovary color*.—Ovary non-visible.

Fruit and seed set: Nut-like, surrounded by 2 involucral bracts, typical for *Corylus*, shaped irregular obovate, base cuneate, apex incised to deeply incised, margins entire to dentate-serrate.

*Involucral bracts*.—Two bracts per fruit.
*Length*.—Average 3.6 cm (including involucral bracts).
*Diameter*.—Average 2.8 cm (including involucral bracts).
*Nut color*.—RHS 165B to 199D.
*Fruit coloration*.—Involucral bracts greyed-purple, RHS 183A and RHS 183B fading to brown towards base RHS 200A to RHS 200B.
*Number of fruits per cluster*.—Three to five.
*Fruit texture*.—Involucral bracts covered with short bristly hairs, average length of hairs 0.8 mm colored grey-orange near RHS 171A.
*Quantity of fruit per plant*.—Average 8.
*Nut color*.—Greyed-orange; 165B, top grey-brown; 199D and lighter.
*Average number of days for fruit ripening*.—7 months.
*Nut shape*.—Flattened orbicular to near reniform.
*Nut length*.—Average 1.7 cm.
*Nut diameter*.—Average at widest: 1.5 cm. Average at narrowest: 1.3 cm.
*Nut thickness*.—Average 0.2 cm.
*Individual nut weight*.—Average 1.25 grams.
*Average number of stripes on the shell*.—32.
*Size of fruit pistil scar on the shell*.—Average 0.1 cm by 0.3 cm, shaped broad acute.
*Curvature of the nut basal scar*.—Average diameter of nut basal scar is 1.1 cm, medium curvature, margins of basal scar an average of 0.4 cm lower than the top.
*Quantity of kernels per fruit*.—Average one (please note that kernels are not present each year fruit is produced).
*Kernel length*.—Average 1.3 cm.
*Kernel diameter*.—Average 1.1 cm.
*Kernel texture*.—Smooth, slightly glossy, and glabrous.
*Kernel color*.—RHS 164B.
*Color of fiber on the keel*.—RHS 165C (greyed-orange).
*Color of pellicle under the fiber*.—RHS 199B and N199D (a blend of grey-brown).

Disease and pest/insect resistance: Similar to other *Corylus* varieties.

Temperature tolerance: Unknown but hardy to USDA zone 5 (−23° C.) and tolerant to temperatures up to USDA zone 9 (40° C.).

COMPARISION WITH THE FEMALE PARENT (ALSO CLOSES KNOWN VARIETY)

'BWM01' is most similar to the commercial *Corylus* 'Maxima Purpurea' (Unpatented) Differences between the varieties are described in Table 1.

TABLE 1

| Comparison with Female parent | | |
|---|---|---|
| Characteristic | 'BWM01' | 'Maxima Purpurea' |
| Leaf color | Leaf color of greyed-purple, black, purple and brown. | Red changing to green |

I claim:

1. A new and distinct cultivar of *Corylus* Plant Named 'BWM01' as described and illustrated herein.

* * * * *